United States Patent [19]

Bellina et al.

[11] 4,053,634

[45] Oct. 11, 1977

[54] MITICIDAL AND APHICIDAL METHOD UTILIZING 2-HIGHER ALKYL-3-HYDROXY-1,4-NAPHTHOQUINONE CARBOXYLIC ACID ESTERS

[75] Inventors: Russell Frank Bellina; Dennis Lynn Fost, both of Wilmington, Del.

[73] Assignee: E. I. Du Pont de Nemours and Company, Wilmington, Del.

[21] Appl. No.: 722,513

[22] Filed: Sept. 13, 1976

Related U.S. Application Data

[60] Division of Ser. No. 613,553, Sept. 15, 1975, which is a continuation-in-part of Ser. No. 531,483, Dec. 11, 1974, abandoned, which is a continuation-in-part of Ser. No. 494,294, Aug. 2, 1974, abandoned, which is a continuation-in-part of Ser. No. 468,692, May 10, 1974, abandoned.

[51] Int. Cl.[2] .................. A01N 9/24

[52] U.S. Cl. .................. 424/312; 260/396 R; 424/301; 424/305; 424/311; 424/313; 424/314

[58] Field of Search .................. 424/312, 305; 260/396 R

[56] References Cited

U.S. PATENT DOCUMENTS

| | | | |
|---|---|---|---|
| 2,553,647 | 5/1951 | Fieser et al. | 260/396 |
| 2,553,648 | 5/1951 | Fieser et al. | 260/396 |
| 2,572,946 | 10/1951 | Paulshock | 424/331 |

OTHER PUBLICATIONS

J. Econ. Ent., 1962 55, pp. 737–743, Chapman et al.
Nakanishi et al., J.A.C.S., 1952, pp. 3910–3915.

*Primary Examiner*—Allen J. Robinson

[57] ABSTRACT

This invention relates to a novel pesticidal, e.g., miticidal and aphicidal, method utilizing an active ingredient which is represented by the following formula:

I

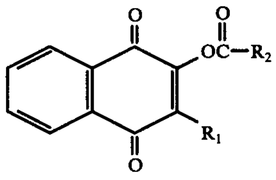

wherein $R_1$ is alkyl of 8–14 carbon atoms either branched, cyclic or straight chain; and $R_2$ is alkyl of 1–17 carbon atoms either branched or straight chain, alkenyl of 2–17 carbon atoms, cycloalkyl of 3–6 carbon atoms, alkoxy of 1–4 carbon atoms, $-CH_2OCH_3$, $-CH_2OCH_2CH_3$ or $-CH=CH-CO_2H$.

7 Claims, No Drawings

MITICIDAL AND APHICIDAL METHOD UTILIZING 2-HIGHER ALKYL-3-HYDROXY-1,4-NAPHTHOQUINONE CARBOXYLIC ACID ESTERS

CROSS-REFERENCE TO RELATED APPLICATIONS

This is a division of copending application Ser. No. 613,553, filed Sept. 15, 1975, which is a continuation-in-part of our copending application Ser. No. 531,483, filed Dec. 11, 1974 (now abandoned), which in turn is a continuation-in-part of our copending application Ser. No. 494,294, filed Aug. 2, 1974, (now abandoned), which in turn is a continuation-in-part of our copending application Ser. No. 468,692, filed May 10, 1974 (now abandoned).

BACKGROUND OF THE INVENTION

This invention relates to miticidal and aphicidal methods using 2-higher alkyl-3-hydroxy-1,4-naphthoquinone esters.

U.S. Pat. Nos. 2,553,647 and 2,553,648 disclose broadly 2-alkyl-3-hydroxy-1,4naphthoquinones and their corresponding ester derivatives. These compounds are described as having antagonistic action against organisms which cause malarial infections.

U.S. Pat. No. 2,572,946 discloses the use of non-acylated compounds as miticides; it contains no teaching of acylated compounds.

Nakanishi et al. JACS 1952, 3910–3915 discloses the n-undecyl analog of 2-alkyl-3-acetoxy-1,4-naphthoquinone. No use for the composition is disclosed.

SUMMARY OF THE INVENTION

This invention is a method for controlling mites or aphids by applying to a locus to be protected, preferably a plant, a miticidal or aphicidal amount of a compound of the formula:

I

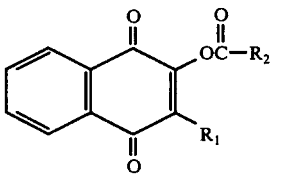

wherein $R_1$ is alkyl of 8–14 carbon atoms which are branched, cyclic, or straight chain and $R_2$ is alkyl or 1–17 carbon atoms either branched or straight chain, alkenyl of 2–17 carbon atoms, cycloalkyl of 3–6 carbon atoms, alkoxy of 1–4 carbon atoms, $-CH_2OCH_3$, $-CH_2OCH_2CH_3$ or $-CH=CH-CO_2H$.

The compounds of Formula I are miticides and aphicides. That is to say, when an effective amount of such compounds is brought into contact with mites or aphids, these pests are killed. The compounds are thus useful for protecting plants and animals from damage caused by mites or aphids.

The invention also includes miticidal and aphicidal compositions which contain at least one compound of Formula I as active ingredient.

Preferred for their ease of synthesis are those compounds of Formula I where $R_1$ is straight chain alkyl of 8–14 carbon atoms.

More preferred for their greater biological activity are those compounds of Formula I where $R_1$ is straight chain alkyl or 11–14 carbon atoms;

It is preferred that $R_2$ is alkyl of 1–6 carbon atoms, more preferably straight chain of 1–6 carbon atoms, alkenyl of 2 to 3 carbon atoms, methoxy or ethoxy, most preferably ethyl or methyl. Specifically, the following compounds are preferred for their highest miticidal and aphicidal activity:

3-acetoxy-2-n-tetradecyl-1,4-naphthoquinone;
3-acetoxy-2-n-dodecyl-1,4-naphthoquinone;
3-propionyloxy-2-n-tetradecyl-1,4-naphthoquinone;
2-n-dodecyl-3-propionyloxy-1,4-naphthoquinone;
3-butyryloxy-2-n-tetradecyl-1,4-naphthoquinone;
2-n-dodecyl-3-methoxycarbonyloxy-1,4-naphthoquinone;
2-n-dodecyl-3-ethoxycarbonyloxy-1,4-naphthoquinone;
3-butyryloxy-2-n-dodecyl-1,4-naphthoquinone;
2-n-dodecyl-3-isobutyryloxy-1,4-naphthoquinone;

In a specific embodiment of the instant invention, the compounds of the instant invention are applied in admixture with a superior oil, preferably a minor amount of superior oil, e.g., less than 5% by weight. The resulting miticidal activity is greater than the additive results. Superior oils are discussed in Chapman et al., *Selection of a Plant Spray Oil Combining Full Pesticidal Efficiency with Minimum Plant Injury Hazards,* Jour. Econ. Ent., 1962, 55:737–43, the disclosure of which is herein incorporated by reference. The resulting mixture of the compound and the superior oil is novel.

DESCRIPTION OF THE INVENTION

Synthesis

The compounds of Formula I can be prepared by the procedures described in the previously cited *J. Am. Chem. Soc.* article and in U. S. Pat. Nos. 2,553,647 and '648. The final step in the synthesis may be accomplished by treating the corresponding 2-alkyl-3-hydroxy-1,4-napthoquinone with the appropriate acid chloride or anhydride in the presence of at least an equivalent of an amine such as pyridine or triethylamine, or by treating the sale of the 2-alkyl-3-hydroxy-1,4-naphthoquinone with the appropriate acid chloride or anhydride in an inert solvent. The following examples are given to illustrate the above-described processes.

EXAMPLE 1

Preparation of 3-Acetoxy-2-n-dodecyl-1,4-naphthoquinone

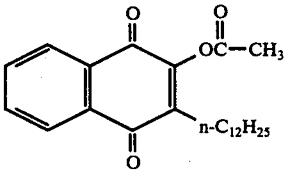

A mixture of 2.0 parts of 2-n-dodecyl-3-hydroxy-1,4-naphthoquinone, 0.81 parts of triethylamine, 0.63 parts of acetyl chloride and 50 parts of methylene chloride was stirred at room temperature for 30 hours. The resulting mixture was distributed between methylene chloride and water. The methylene chloride layer was separated, dried over magnesium sulfate, then filtered and evaporated under reduced pressure. The residue was crystallized from petroleum ether (b.p. 30°-60°) to give 1.2 parts of 3-acetoxy-2-n-dodecyl-1,4-naphthoquinone, m.p.57°-58° C.

EXAMPLE 2

Preparation of 2-n-Dodecyl-3-propionyloxy-1,4-naphthoquinone

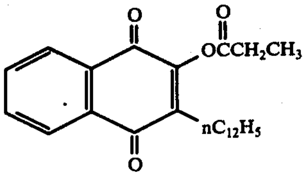

A mixture of 4.0 parts of 2-n-dodecyl-3-hydroxy-1,4-naphthoquinone, 4.4 parts of propionic anhydride, and 50 parts of pyridine was stirred at room temperature for 16 hours. The resulting mixture was evaporated under reduced pressure to remove the pyridine. The residue was crystallized from methanol to give 2.9 parts of 2-n-dodecyl-3-propionyloxy-1,4-naphthoquinone, m.p. 42°-44° C.

EXAMPLE 3

Preparation of the Sodium Salt of 2-n-Dodecyl-3-hydroxy-1,4-naphthoquinone

A dispersion of 1.9 parts of sodium hydride in 250 parts of tetrahydrofuran was added to a solution of 26 parts of 2-n-dodecyl-3-hydroxy-1,4-naphthoquinone in 450 parts of tetrahydrofuran at room temperature. The mixture was stirred at room temperature for 1 hour, then filtered to give a burgundy solution of the sodium salt.

EXAMPLE 4

Preparation of 2-n-Dodecyl-3-methoxycarbonyloxy-1,4-naphthoquinone

Sixty parts of the above-mentioned sodium salt solution was stirred with 0.59 parts of methyl chloroformate in 10 parts of tetrahydrofuran at room temperature. The mixture was stirred for 1 hour, then allowed to stand overnight. The resulting suspension was filtered and the filtrate evaporated to dryness. The residue was crystallized from acetonitrile to give 2.0 parts of 2-n-dodecyl-3-methoxycarbonyloxy-1,4-naphthoquinone, m.p. 70°-72° C.

By using the appropriate 2-alkyl-3-hydroxy-1,4-naphthoquinone and the appropriate acid chloride or anhydride, the following compounds shown in Table I could be similarly prepared by anyone skilled in the art, using the procedure outlined in Examples 1 through 4.

Table 1

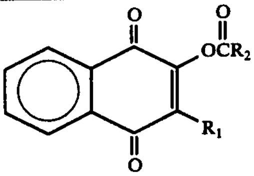

| $R_1$ | $R_2$ | Melting Point (° C.) |
|---|---|---|
| $-n-C_8H_{17}$ | $-n-C_3H_7$ | |
| $-n-C_9H_{19}$ | $-C_2H_5$ | |
| $-C_{11}H_{23}$ | $-CH_3$ | 51-53 |
| $-n-C_{11}H_{23}$ | $-CH_2CH_3$ | $N_D^{25}$ 1.5209 |
| $-n-C_{11}H_{23}$ | $-CH_2CH_2CH_3$ | $N_D^{25}$ 1.5131 |
| $-n-C_{11}H_{23}$ | $-CH(CH_3)_2$ | $N_D^{25}$ 1.5155 |
| $-n-C_{12}H_{25}$ | $-CH_3$ | 57-58 |
| $-n-C_{12}H_{25}$ | $-CH_2CH_3$ | 42-44 |
| $-n-C_{12}H_{25}$ | $-CH_2CH_2CH_3$ | $N_D^{25}$ 1.5120 |
| $-n-C_{13}H_{27}$ | $-CH_3$ | 58-60 |
| $-CH(CH_3)-CH_2-C_9H_{19}$ | $-CH_3$ | $N_D^{25}$ 1.5332 |
| $-(CH_2)_9-CH(CH_3)_2$ | $-CH(CH_3)-CH_3$ | |
| $-(CH_2)_3-$ 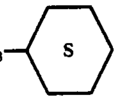 | $-CH_3$ | 72-74 |

Table 1-continued

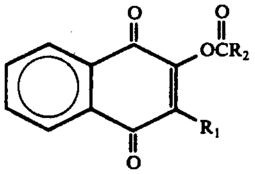

| $R_1$ | $R_2$ | Melting Point (° C.) |
|---|---|---|
| 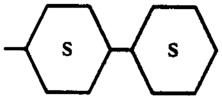 | $-CH_3$ | |
| $-n\text{-}C_{14}H_{29}$ | $-CH_3$ | 62–63 |
| $-n\text{-}C_{12}H_{25}$ | $-CH(CH_3)_2$ | $N_D^{25}$ 1.5157 |
| $-n\text{-}C_{10}H_{21}$ | $-CH_3$ | |
| $-n\text{-}C_{14}H_{29}$ | $CH_2CH_3$ | 52–53° |
| $-n\text{-}C_{14}H_{29}$ | $CH_2CH_2CH_3$ | 40–41° |
| $-C_{14}H_{29}$ | 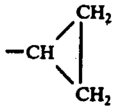 | 65–67° |
| $-n\text{-}C_{12}H_{25}$ | 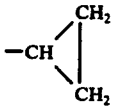 | 59–61 |
| $-n\text{-}C_{12}H_{25}$ | 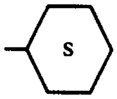 | 50–52 |
| $-n\text{-}C_{12}H_{25}$ | 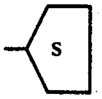 | |
| $-n\text{-}C_{12}H_{25}$ | $-(CH_2)_4CH_3$ | $N_D^{25}$ 1.5133 |
| $-n\text{-}C_{12}H_{25}$ | $-C(CH_3)_3$ | $N_D^{25}$ 1.5133 |
| $-n\text{-}C_{12}H_{25}$ | $-OCH_3$ | 70–72 |
| $-n\text{-}C_{12}H_{25}$ | $-OCH_2CH_3$ | 42–47 |
| $-n\text{-}C_{12}H_{25}$ | 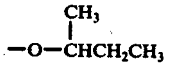 | [IR>=o 1753 $cm^{-1}$] |
| $-n\text{-}C_{12}H_{25}$ | $-CH_2OCH_3$ | 69–71 |
| $-n\text{-}C_{12}H_{25}$ | $-CH_2OCH_2CH_3$ | |
| $-n\text{-}C_{12}H_{25}$ | $-(CH_2)_7CH_3$ | [IR>=o 1791 $cm^{-1}$] |
| $-n\text{-}C_{12}H_{25}$ | $-(CH_2)_{12}CH_3$ | 51–53 |
| $-n\text{-}C_{12}H_{25}$ | $-(CH_2)_{16}CH_3$ | |
| $-n\text{-}C_{12}H_{25}$ | $-CH{=}CH_2$ | |
| $-n\text{-}C_{12}H_{25}$ | $-CH{=}CHCH_3$ | 43.5–44.5 |
| $-n\text{-}C_{12}H_{25}$ | 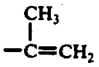 | $N_D^{25}$ 1.5202 |
| $-n\text{-}C_{12}H_{25}$ | $-CH{=}CH-CO_2H$ | $N_D^{25}$ 1.5162 |
| $-n\text{-}C_{12}H_{25}$ | $-CH{=}CH-CH{=}CH-CH_3$ | 68–74 |
| $-n\text{-}C_{12}H_{25}$ | $-(CH_2)_7CH{=}CHCH_2CH{=}CH(CH_2)_4CH_3$ | |

Table 1-continued

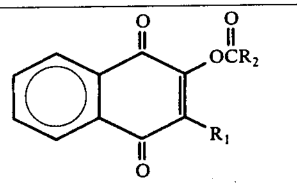

| $R_1$ | $R_2$ | Melting Point (° C.) |
|---|---|---|
| $-CH_2CH_2-$ 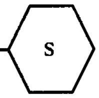 | $-CH_3$ | 68-69 |
| $n-C_{12}H_{25}$ | $-(CH_2)_5CH_3$ | $N_D^{25}$ 1.5141 |
| $n-C_{12}H_{25}$ | $-(CH_2)_6CH_3$ | 54-57 |
| $-CH_2-$ 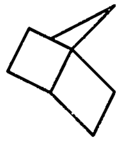 | $-CH_3$ | 91-93 |
| $-n-C_{12}H_{25}$ | $-(CH_2)_7-CH=CH-(CH_2)_7CH_3$ | |

The method of preparation of the compounds is not critical to the instant invention.

Formulation and Use

The compounds of Formula I are useful as miticides and can be used to protect both plants and animals from damage caused by these pests. More specifically, fruits, field crops, vegetables, ornamentals, birds and other warm-blooded animals including man can also be protected.

When mites come into contact with the compounds of Formula I, either in the form of direct sprays or by walking over surfaces which have been treated, they rapidly become irritated and leave the area or are killed if they have been exposed to a sufficiently high dosage. While most plants or animals are able to tolerate the presence of very small numbers of mites without apparent adverse effect, the reproductive capacity of these pests is enormous. Generally, mite populations rapidly build up, easily outstripping parasite and predator capabilities for control. Growers noting rapid mite build-up must take immediate action to prevent damage to economically important crops. Thus, a method is needed for immediately reducing mite build-up and thereby preventing damage to important crops or animals.

Similarly the compounds of Formula I are also useful as aphicides and can be used to protect fruits, field and vegetable crops, ornamentals, and other plants from aphid attack. When applied to aphids or to the locus of aphid infestation, these pests are killed or driven from the plants.

The method of this invention, namely contact mites or aphids with a miticidally or aphicidally effective concentration of Formula I, is a most desirable method for control of these pests. For instance, very small quantities of compounds of Formula I are required for miticidal or aphicidal activity; additionally, the compounds are not rapidly washed from leaves by rain. They do not have any adverse effect on ladybird beetles, which are important mite and aphid predators, and the compounds rapidly degrade in the environment. The compounds are also effective against phosphorus-resistant strains of mites.

The quantity of compound needed for miticidal or aphicidal activity will vary depending on the specific situation. Among the variables that must be considered in deciding on the quantity of chemical to be used are the specific compound itself, the specific mite or aphid to be controlled, weather conditions, the type or crop, the stage of development of the crop, the volume of spray applied, population pressure, and the interval between applications. For plant protection, solutions or suspensions containing as little as 5 ppm of active ingredient in a spray solution may prove effective under a given set of circumstances. For field usage, however, in high-volume applications, aqueous spray preparations containing 40–4,000 ppm of active ingredient are generally useful. Preferred are suspensions containing 80–1,000 ppm, and most preferred are those containing 150–500 ppm. On an area basis, in general, 0.03 to 15 kilograms of active ingredient per hectare are acceptable, preferably 0.06 to 8 kilograms, and most preferably 0.1 to 4 kg. When applied in an orchard, spraying is continued until run-off is observed.

It may be desirable or useful to mix the compounds of this invention with other agricultural pesticides or adjuvants. Such mixtures often increase the effectiveness of the application on mites and broaden the scope of control to embrace other pests such as insects, fungi, nematodes, or bacteria. A mixture with a refined petroleum spray oil or superior oil has been shown to provide greater than additive results on mites. Other pesticides with which the compounds of this invention may be mixed to achieve broader-spectrum activity include:

diazinon — 0,0-diethyl 0-(2-isopropyl-4-methyl-6-pyrimidyl)phosphorothioate disulfoton — 0,0-diethyl S-2-(ethylthio)ethylphosphorodithioate phorate — 0,0-diethyl S-(ethylthio)methylphosphorodithioate oxamyl — S-methyl 1-(dimethylcarbamoyl)-N-[(methylcarbamoyl)oxy]thioformimidate
methomyl — S-methyl N-(methylcarbamoyloxy)thioacetimidate
benomyl — 1-butylcarbamoyl-2-benzimidazolecarbamic acid, methyl ester
captan — N—-trichloromethylthiophthalimide
maneb — ethylenebisdithiocarbamic acid, manganese salt
carboxin — 5,6-dihydro-2-methyl-1,4-oxathiin-3-carboxanilide
streptomycin — 2,4-diguanidino-3,5,6-trihydroxycyclohexyl-5-deoxy-2-o-(2-deoxy-2-methylamino-α-glycopyranosyl)-3-formylpentofuranoside The compounds are especially suited for the protection of living plants such as fruit-bearing trees, nut-bearing trees, ornamental trees, forest trees, vegetable crops, horticultural crops (including ornamentals, small fruit and berries) and grain and seed crops. Apple trees, peach trees, cotton, citrus trees, beans and peanuts are particularly susceptible to mite or aphid damage and can be protected by application of the compounds of this invention. To assure control throughout the growing season (e.g., June through August in the Northern Hemisphere) multiple applications at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites," and which attack a great many deciduous trees, such as apple, pear, cherry, plum and peach trees; *Tetranychus atlanticus* (Atlantic or strawberry mite), *T. cinnabarinus* (carmine spider mite) and *T. pacificus (Pacific mite); which attach cotton and numerous other crop plants; Paratetranychus citri* (citrus red mite) and others which attack citrus; *Phyllocoptruta oleivora* which causes citrus rust; *Bryobia praetiosa* (clover mite) which attacks clover, alfalfa and other crops; and *Aceria neocynodomis* which attacks grasses and other plants.

Aphids controlled by the compounds of this invention include but are not limited to the black bean aphid, *Aphis fabae;* the green peach aphid, *Myzus persicae;* the apple aphid, *Aphis pomi;* the rosy apple aphid, *Anuraphis roseus;* the potato aphid, *Macrosiphum euphorbiae;* the green bug, Toxoptera graminum; cabbage aphid, *Brevicoryne brassicae* and green citrus aphid, *Aphis spiraecola.*

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1 to 99% by weight of active ingredient(s) and at least one of a) about 0.1 to 20% surfactant(s) and b) about 5 to 99% solid or liquid diluent(s). More specifically, they will contain these ingredients in the following approximate proportions:

Table 2

| | Active Ingredient | Diluent(s) | Surfactant(s) |
|---|---|---|---|
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0- 5 |
| Granules & Pellets | 1-95 | 5-99 | 0-15 |
| High-strength Compositions | 90-99 | 0-10 | 0- 2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers," Second Ed., Dorland Books, Caldwell, N.J. The more absorptive diluents are preferred for wettable powders and the denser ones for dusts. Typical liquid diluents and solvents are described in Marsden, "Solvents Guide", Second Edn., Interscience, New York, 1950. Solubility under 0.1% is preferred for suspension concentrates; solution concentrates are preferably stable against phase separation at 0° C. "McCutcheon's Detergents and Emulsifiers Annual," Allured Publ. Corp., Ridgewood, New Jersey, as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine, solid compositions are made by blending and, usually, grinding as in a hammer mill or fluid energy mill. Suspensions are prepared by wet-milling (see, i.e., Littler U.S. Pat. No. 3,060,084). Granules and pellets may be made by spraying the active material upon preformed granular carriers or by agglomeration techniques. See J. E. Browning, "Agglomeration," *Chemical Engineering,* Dec. 4, 1967, pp. 147 ff. and Perry's *Chemical Engineer's Handbook,* Fourth Ed., McGraw-Hill, N.Y., 1963, pp. 8-59 ff.

For further information regarding the art of formulation, see for example:

J. B. Buchanan, U.S. Pat. No. 3,576,834, Apr. 27, 1971, Col. 5 Line 36 through Col. 7 Line 70 and Ex. 1-4, 17, 106, 123-140.

R. R. Shaffer, U.S. Pat. No. 3,560,616, Feb. 2, 1971, Col. 3 Line 48 through Col. 7 Line 26 and Examples 3-9, 11-18.

E. Somers, "Formulation," Chapter 6 in Torgeson, "Fungicides," Vol. I, Academic Press, New York, 1967.

Still another liquid formulation which is particularly convenient for small-scale use is the "aerosol" formulation which is packaged under pressure in a suitable container. The active ingredient may be present in a suspension, emulsion or solution. For simplicity in preparation and use, solutions are preferred. The pressure may be supplied by low-boiling liquids such as propane or chloro-fluoro carbons or by relatively soluble gases such as carbon dioxide or nitrous oxide. The chlorofluoro carbons are preferred for a combination of good solvent power and lack of flammability.

Miticidal ability of the compounds of Formula I is illustrated in the following examples.

EXAMPLE 5

Test units consisted of plant pots containing two red kidney bean plants in the two-leaf stage per pot. The plants were infested with two-spotted mites and sprayed to run-off with solutions of the compounds of this invention. Solutions were made by dissolving weighted quantities of the active ingredients in 10 ml of acetone and then diluting to volume with water containing 1:3000 of a surfactant, TREM 014*. Mortality was evaluated 2 days after spraying.

*TREM 014 is a trade name of the Nopco Chemical Company for a polyhydric alcohol ester.

Table 3

Compounds

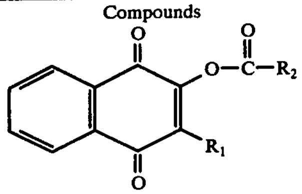

| $R_1$ | $R_2$ | % Mite Mortality at Indicated % Spray Concentration .005 | .002 | .001 | .0005 | .00025 |
|---|---|---|---|---|---|---|
| n-$C_{12}H_{25}$ | $-CH_3$ | | 100 | 100 | 100 | 60 |
| n-$C_{12}H_{25}$ | $-CH_2CH_3$ | 100 | 100 | 99 | 90 | 56 |
| n-$C_{12}H_{25}$ | $-CH_2CH_2CH_3$ | 100 | 100 | 99 | | |
| n-$C_{12}H_{25}$ | $-CH(CH_3)_2$ | 100 | 100 | 99 | | |
| n-$C_{12}H_{23}$ | $-CH_3$ | 99 | 98 | 98 | 45 | 26 |
| n-$C_{11}H_{23}$ | $-CH_2CH_3$ | 100 | 92 | | | |
| n-$C_{11}H_{23}$ | $-CH(CH_3)_2$ | 100 | 94 | 94 | | |
| n-$C_{12}H_{25}$ | 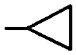 | 100 | 100 | 100 | 98 | 44 |
| n-$C_{12}H_{25}$ | $-C(CH_3)_3$ | 100 | 100 | — | 65 | |
| n-$C_{12}H_{25}$ | $-(CH_2)_4CH_3$ | 100 | 100 | 99 | 93 | 41 |
| n-$C_{12}H_{25}$ | $-(CH_2)_5CH_3$ | 100 | 100 | — | 70 | |

EXAMPLE 6

Bean plants were sprayed to run-off with the indicated concentrations of 3-acetoxy-2-n-dodecyl-1,4-naphthoquinone in TREM 014:water at 1:3000. Sprayed plants were allowed to stand for 3 days prior to infestation with two-spotted mites. Evaluations were made at one and eleven days after infestation.

| % Spray Concentration | % Control After 1 Day | % Control After 11 Days |
|---|---|---|
| .01 | 99 | 100 |
| .005 | 90 | 100 |
| .002 | 58 | mites building up |

EXAMPLE 7

Bean plants were sprayed to run-off with the indicated concentrations of 3-acetoxy-2-n-dodecyl-1,4-naphthoquinone in TREM 014:water at 1:3000. Sprayed plants were allowed to stand for 3 days and then subjected to 7 mm of rain. After drying, the plants were infested with two-spotted mites. Evaluations were made at 1 and 11 days after infestation.

| % Spray Concentration | % Control After 1 Day | % Control After 11 Days |
|---|---|---|
| .01 | 97 | 100 |
| .005 | 94 | 99 |

-continued

| % Spray Concentration | % Control After 1 Day | % Control After 11 Days |
|---|---|---|
| .002 | 42 | out of control |

EXAMPLE 8

Apple seedlings approximately 13 cm in height were infested with European red mites and then sprayed to run-off with the indicated concentrations of 3-acetoxy-2-n-dodecyl-1,4-naphthoquinone in TREM 014:water at 1:3000. Evaluations were made two days after spraying.

| % Spray Concentration | % Kill |
|---|---|
| .005 | 100 |
| .002 | 100 |
| .001 | 100 |
| .0005 | 95 |

EXAMPLE 9

Red kidney bean plants infested with two-spotted mites were sprayed with 3-acetoxy-2-n-dodecyl-1,4-naphthoquinone alone and in combination with 1% UNICO* spray oil. Evaluations are averages of three replicates and were made 2 days after spraying. These results show that greater than additive effects are obtained by using the compounds of the invention in combination with a spray oil.

| Compound | % Spray Concentration | % Mortality |
|---|---|---|
| 2-acetoxy-3-dodecyl-1,4-napthoquinone | .002 | 100 |
| | .001 | 99 |
| | .0005 | 86 |
| | .00025 | 23 |
| | .0001 | 2 |
| 2-acetoxy-3-dodecyl-1,4-naphthoquinone + 1% UNICO* oil in spray solution | .002 | 100 |
| | .001 | 100 |
| | .0005 | 100 |
| | .00025 | 97 |
| | .0001 | 60 |
| 1% UNICO* spray oil | | 0 |

*UNICO is a trade name of United Co-operatives, Inc., of Alliance, Ohio. It is a -continued

| Compound | % Spray Concentration | % Mortality |
|---|---|---|

refined petroleum distillate containing about 3% inert ingredients and is classified as a superior oil.

EXAMPLE 10

Red kidney bean plants in the two-leaf stage were sprayed to run-off with solutions of 2-dodecyl-3-acetoxy-1,4-naphthoquinone at concentrations of 10, 5 and 2.5 ppm. The plants were allowed to dry. Two sets containing two replicates of each rate were formed. One set was infested with normal 2-spotted mites and the other with a methyl parathion-resistant strain. The data are set forth below and indicate that phosphorus-resistant strains of mites are equally susceptible as normal mites to the compounds of this invention.

| Concentration of Active Ingredient (%) | % Kill of Mites in 48 Hours: Normal Mites | % Kill of Mites in 48 Hours: Phosphorus-Resistant Mites |
|---|---|---|
| .001 | 100 | 100 |
| .0005 | 80 | 81 |

Aphicidal properties of the compounds of Formula I are illustrated in the following examples.

EXAMPLE 11

Potted nasturtium plants infested with the black bean aphid were sprayed on a rotating turntable with 2-acetoxy-3-dodecyl-1,4-naphthoquinone at concentrations of 100, 50, and 25 ppm. Mortality counts were made 72 hours after spraying, with the results indicated below.

| % Spray Concentration | % Kill |
|---|---|
| .01 | 100 |
| .005 | 100 |
| .0025 | 89 |

EXAMPLE 12

Solutions of the compounds of this invention were sprayed at a concentration of 150 ppm on potted nasturtium plants infested with the black bean aphid. Sprays were applied to run-off with a hand-held "Son-of-a-Gun" ® sprayer. Du Pont L-144-WDG was included at 1:2000 in the sprays as a wetting agent. Mortality counts were made at the end of 24 hours.

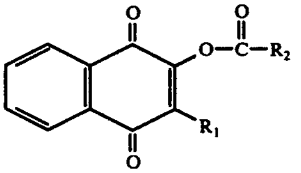

| $R_1$ | $R_2$ | % Aphid Mortality |
|---|---|---|
| $C_{12}H_{25}$ | $-CH_3$ | 100 |
| $C_{14}H_{29}$ | $-CH_3$ | 99 |
| $C_{12}H_{25}$ | $-CH_2CH_3$ | 98 |
| $C_{14}H_{29}$ | $-CH_2CH_3$ | 99 |

-continued

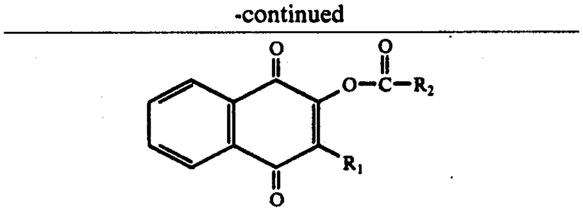

| $R_1$ | $R_2$ | % Aphid Mortality |
|---|---|---|
| $C_{12}H_{25}$ | 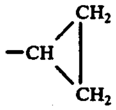 | 97 |
| $C_{14}H_{29}$ | 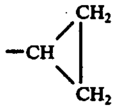 | 93 |
| $C_{12}H_{25}$ | $-CH_2CH_2CH_3$ | 98 |
| $C_{14}H_{29}$ | $-CH_2CH_2CH_3$ | 87 |

EXAMPLE 13

Green peach aphids on discs cut from Chinese cabbage leaves were sprayed on a turn-table spray rig with acetone solutions of the compounds of this invention. The leaf discs were held under constant environmental conditions for 24 hours at which time mortality counts were made. The concentrations used and percent aphid kill are tabulated below.

Table 4

Compounds

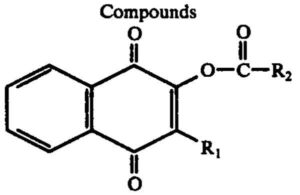

| $R_1$ | $R_2$ | % Aphid Mortality at % Spray Concentration of .1 | .05 | .01 | .005 |
|---|---|---|---|---|---|
| $C_{12}H_{25}$ | $-CH_3$ | 100 | 100 | 90 | 86 |
| $C_{14}H_{29}$ | $-CH_3$ | 100 | 89 | 85 | 69 |
| $C_{12}H_{25}$ | $-CH_2CH_3$ | 100 | 100 | 94 | 84 |
| $C_{14}H_{29}$ | $-CH_2CH_3$ | 100 | 100 | 98 | 83 |
| $C_{12}H_{25}$ | 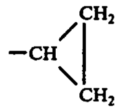 | 100 | 100 | 88 | 71 |
| $C_{14}H_{29}$ | 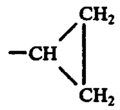 | 97 | 66 | 80 | 25 |
| $C_{12}H_{25}$ | $-CH_2CH_2CH_3$ | 100 | 100 | 83 | 75 |
| $C_{14}H_{29}$ | $-CH_2CH_2CH_3$ | 100 | 100 | 93 | 79 |

EXAMPLE 14

A 25% emulsifiable composition of 2-acetoxy-3-dodecyl-1,4-naphthoquinone was applied with commercial equipment to dwarf Golden Delicious apple trees in a Delaware orchard. Application was made four times at weekly intervals, starting May 8, at rates of 0.5, 1, and 4 oz/100 gallons. Counts made 3 days after the last spray showed excellent control of the apple aphid as indicated below. There was an average of 573 aphids per terminal in unsprayed control trees.

| Spray Concentration OZ/100 gals. | % Control of Apple Aphid |
|---|---|
| 0.5 | 93.7 |
| 1 | 97.6 |
| 4 | 99.8 |

EXAMPLE 15

Tests units consisting of plant pots containing two red kidney bean plants in the 2-leaf stage were infested with 2-spotted mites and sprayed to run-off with solutions/suspensions of the compounds of this invention. Solutions/suspensions were made by dissolving weighed quantities of the active ingredients in 10 ml of acetone and then diluting to volume with water containing TREM 014 at 1:3000. Mortality was evaluated two days after spraying.

Table 5

Compounds

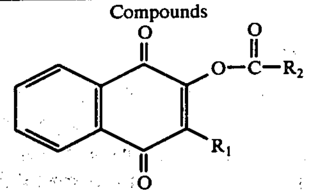

| $R_1$ | $R_2$ | % Mortality at .002% Spray Concentrations |
|---|---|---|
| n-$C_{12}H_{25}$ | $-(CH_2)_7CH_3$ | 96 |
| n-$C_{12}H_{25}$ | $-(CH_2)_{12}CH_3$ | 99 |
| n-$C_{12}H_{25}$ | $-CH=CHCH_3$ | 100 |
| n-$C_{12}H_{25}$ | $-CH=CHCH=CHCH_3$ | 98 |
| n-$C_{12}H_{25}$ | $-OCH_3$ | 100 |
| n-$C_{12}H_{25}$ | $-OC_2H_5$ | 99 |
| n-$C_{12}H_{25}$ | $-CH_2-O-CH_3$ | 97 |
| n-$C_{12}H_{25}$ | $-CH=CHCOOH$ | 100 |
| n-$C_{13}H_{27}$ | $-CH_3$ | 99 |
| n-$C_{12}H_{25}$ | 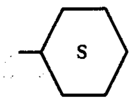 | 93 |
| n-$C_{12}H_{25}$ | $-OCHCH_2CH_3$<br>\|<br>$CH_3$ | 60 |

EXAMPLE 16

European red mite infestations were monitored on apple trees in an orchard near Newark, Delaware. When counts indicated that the number of mites per leaf had exceeded the grower-acceptable level of 5/leaf, the trees were sprayed with a compound of the invention. Four replicate sets of trees were each sprayed with 3-acetoxy-2-n-dodecyl-1,4-naphthoquinone at 14, 28 and 112 g/400 l concentration levels following grower practices. Sprays were again applied 6 days later. The number of mites present per leaf was rapidly reduced below the economic mite damage level (5 mites/leaf) by all treatments. All treated trees remained healthy, vigorous, and free of observable mite damage until the mite population in the remainder of the orchard collapsed of natural causes two weeks later. At that time, leaves of untreated trees were badly russeted by the uncontrolled feeding of the mites while leaves on the treated trees had a healthy, dark green coloration.

We claim:

1. A method for protecting plants from mites or aphids comprising applying to the plant locus to be protected a miticidally or aphicidally effective amount of a compound of the formula:

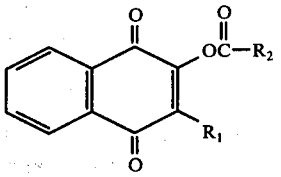

wherein $R_1$ is alkyl of 8–14 carbon atoms which are branched, cyclic, or straight chain and $R_2$ is alkyl of 7–17 carbon atoms either branched or straight chain or cycloalkyl of 3–6 carbon atoms.

2. The method of claim 1 wherein $R_1$ is a straight chain alkyl of 8–14 carbon atoms.

3. The method of claim 1 wherein $R_1$ is a straight chain alkyl of 11–14 carbon atoms.

4. The method of claim 1 wherein $R_1$ is an alkyl of 11–14 carbon atoms either branched or straight chain.

5. The method of claim 1 wherein the locus is selected from the group consisting of apple, citrus, and peach trees, cotton, peanuts, and beans.

6. The method of claim 1 wherein the compound is applied to apple trees at intervals during the growing season.

7. The method of claim 1 wherein said compound is applied in admixture with a superior oil.

* * * * *